United States Patent
Lowry et al.

(10) Patent No.: US 6,376,544 B2
(45) Date of Patent: Apr. 23, 2002

(54) NUTRITIONAL PRODUCT FOR A PERSON HAVING RENAL FAILURE

(75) Inventors: Carol Jo Lowry, Minneapolis; Kathy Marie Sass, Forest Lake, both of MN (US)

(73) Assignee: Novartis Nutrition AG, Berne (CH)

( * ) Notice: Subject to any disclaimer, the term of this patent is extended or adjusted under 35 U.S.C. 154(b) by 0 days.

(21) Appl. No.: 09/775,727

(22) Filed: Feb. 2, 2001

Related U.S. Application Data

(63) Continuation of application No. 09/078,165, filed on May 13, 1998, now Pat. No. 6,288,116.

(51) Int. Cl.$^7$ .............................................. A61K 31/195

(52) U.S. Cl. ...................... 514/565; 562/516; 562/562; 426/648

(58) Field of Search ..................... 514/565; 426/648; 562/516, 562

(56) References Cited

U.S. PATENT DOCUMENTS

| | | | |
|---|---|---|---|
| 4,957,938 A | | 9/1990 | Anderson et al. ........... 514/412 |
| 5,108,767 A | | 4/1992 | Mulchandani et al. ........ 426/72 |
| 5,221,668 A | | 6/1993 | Henningfield et al. ........ 514/23 |
| 5,438,042 A | | 8/1995 | Schmidl et al. ............... 514/21 |
| 5,550,146 A | * | 8/1996 | Acosta et al. ............... 514/400 |
| 5,576,287 A | * | 11/1996 | Zaloga et al. .................. 514/2 |
| 5,714,472 A | * | 2/1998 | Gray et al. ..................... 514/21 |
| 5,719,133 A | * | 2/1998 | Schmidl et al. ............... 514/58 |
| 5,719,134 A | * | 2/1998 | Schmidl et al. ............... 514/58 |
| 5,728,678 A | * | 3/1998 | Trimbo et al. ................. 514/12 |
| 5,731,290 A | * | 3/1998 | Schneider .................... 514/20 |
| 5,776,913 A | * | 7/1998 | Ogilvie et al. ................ 514/57 |
| 5,780,039 A | * | 7/1998 | Greenberg et al. .......... 424/400 |
| 5,780,439 A | * | 7/1998 | Mendy et al. ................. 514/21 |
| 5,874,106 A | * | 2/1999 | Adedotun et al. .......... 424/456 |
| 5,922,766 A | * | 7/1999 | Acosta et al. ............... 514/561 |
| 6,288,116 B1 | * | 9/2001 | Lowry et al. ............... 514/565 |

FOREIGN PATENT DOCUMENTS

| | | | |
|---|---|---|---|
| EP | 0 747 395 | | 12/1996 |
| WO | 95/29675 | | 11/1995 |
| WO | 9733568 | * | 9/1997 |
| WO | 9804256 | * | 2/1998 |
| WO | 9832428 | * | 7/1998 |

OTHER PUBLICATIONS

Berkow et al. (eds.), *The Merck Manual of Diagnosis and Therapy*, 16th Edition, Merck & Co., Rahway, NJ, 1992, only pp. 1661–1668 and 1684–1702 supplied.*

Reyes et al., "Role of Arginine in Health and in Renal Disease," *American Journal of Physiology (Renal, Fluid and Electrolyte Physiology*, vol. 36(3)), 267(No. 3, Pt. 2), F331–F346 (Sep. 1994).*

Derwent Abstracts, 97–299788/28, DE 29703380–UI , Jun. 5, 1997.

Derwent Abstracts, 80–11994C/07,JP 5–5002–625, Jan. 10, 1980.

Derwent Abstracts, 79–69979B/39, BE 876263, Sep. 3, 1979.

Derwent Abstracts, 97–409877/38, JP 09182573–A, Jul. 15, 1997.

Derwent Abstracts, 91–231122/32, DE 4002–204–A , Aug., 1991.

Derwent Abstracts, 89–079981/11, JP 0 1030–558–A, Feb. 1, 1989.

Derwent Abstracts, 89–020278/03, JP 6 3296–663–A, Dec. 2, 1988.

Food Service Resource, Resource Renal Beverage, Novartis Nutrition, 1998, Literature.

O. Mareckova, et al., Czech Med, vol. 4 Nos. 1–2, pp. 81–90 (1981) published PubMed Abstract.

L. Schramm, et al., Ren Fail, vol. 16, No. 5, pp. 555–69 (1994) published PubMed.

PW Sanders, Blood Purif, vol. 13, Nos. 3–4, pp. 219–227 (1995) published PubMed.

* cited by examiner

*Primary Examiner*—James O. Wilson
*Assistant Examiner*—Lawrence E Crane
(74) *Attorney, Agent, or Firm*—Michael U. Lee; John D. Thallemer

(57) ABSTRACT

L-arginine found essential to enhance the glomerular function of the kidneys is used φ formulate a low viscosity, calorie-dense, nutritional product for a person having renal failure. In a product free of citric acid or citrates, for oral ingestion, the taste of arginine is counteracted by lactic, malic or adipic acid; in a formulation for tube-feeding, citric acid and citrates in a specified ratio controls the product's stability. The ratio of calcium to phosphorus is controlled, as is the caloric distribution and water content; the amounts of vitamins and minerals included provide a nutritionally complete formulation.

7 Claims, 2 Drawing Sheets

HEAT WATER HELD IN PROCESSOR 130°-150°F
AND ADD STABILIZER AND ANTIFOAM

↓

ADD CASEINATE, CORN
SYRUP AND FLAVOR

↓ ← MIX LACTIC & L-ARGININE
AND ADD TO PROCESSOR

← MIX OILS, HEAT 160°-165°F
ADD LECITHIN, ADD TO PROCESSOR

↓

ADD VITAMIN/MINERAL PREMIX

↓

HEAT TO 165°F

↓

HOMOGENIZE

↓

COOL AND ADD VITAMIN C

↓

ASEPTICALLY STERILIZE & PACKAGE

FIGURE 1

NUTRITIONAL PRODUCT FOR A PERSON HAVING RENAL FAILURE

This is a continuation of U.S. application Ser. No. 09/078,165 filed on May 13, 1998, now U.S. Pat. No. 6,288,116.

FIELD OF THE INVENTION

This invention relates generally to a nutritionally complete liquid supplement (referred to as "product") for enteral feeding, which has been formulated to address the nutritional needs of persons undergoing renal dialysis because they suffer from renal failure. The product is formulated for persons who suffer from acute or chronic inflammation of kidney tissue; in particular, those who have a dysfunctional glomerulus, which is a cluster of capillaries responsible for the production of urine.

BACKGROUND OF THE INVENTION

It is well established that renal disease affects the nutritional status of a person with renal failure, both directly and indirectly in so many ways, that it is difficult to achieve a caloric goal by controlling the person's diet. Major factors which determine the quality of life for a patient are (a) the nutritional status of the patient when dialysis was commenced; and, (b) the patient's ability to ingest and most efficiently metabolize the nutrition provided. On the reasonable assumption that protein administration may also enhance the rate of recovery from acute renal failure, U.S. Pat. No. 5,576,287 to Zaloga et al claims a method for treating or preventing such failure by feeding the patient meat proteins but fails to teach how elemental arginine, or how much of it, can be added to improve glomerular function; or, how the calcium to phosphorus ratio can be controlled. By "elemental" arginine is meant molecular arginine (MW=174.2) which is soluble in water. Meat proteins elevate the phosphorus level and there is no indication how the calcium content is increased relative to the phosphorus to maintain a Ca/P ratio greater than 1. Calcium is malabsorbed in patients with renal disease, and they require a relatively high dietary intake; phosphorus is poorly excreted, and due to high plasma levels, phosphorus intake must be limited. A ratio greater than 1, on an elemental basis, w/w (weight for weight), helps to optimize the Ca/P balance of a renal patient undergoing dialysis. The '287 composition may also include any other nutrients including amino acids known to have specific renal vasodilator actions.

Numerous considerations relating to the problems of providing a diet which will determine the availability of desirable nutrients are referred to in U.S. Pat. No. 5,108,767 to Mulchandani and need not be reiterated. Health care professionals dealing with a patient undergoing dialysis must cope with the need to replace the function of the kidneys. They refer to arginine as a non-essential amino acid and do not suggest providing it in elemental form. Neither the '287 nor the '767 disclosures provides the requisite motivation to prepare an acceptable renal nutritional supplement with elemental L-arginine.

Choosing a renal diet is complicated because specific nutrient requirements and limitations vary from patients who have acute renal failure to those who have chronic renal failure or end-stage renal disease. The choice depends on the stage of renal disease, the type of treatment prescribed and whether the patient has diabetes (present in up to one half of all renal patients). The challenge is to balance the need to limit the intake of essential nutrients such as phosphorus, potassium and sodium with the need to provide sufficient protein and energy to maintain nutritional health.

The primary nutritional need for patients undergoing hemodialysis or peritoneal dialysis is to maintain metabolic homeostasis (normal functional indices, positive nitrogen balance, and a stable weight) by feeding them, either as a sole or supplemental source of nutrition, a balanced nutritional product, when they need a nutritionally complete product. Particularly since L-arginine, its precursors and its metabolites are deemed to be at the center of the interaction of different metabolic pathways and interorgan communication (see "Role of arginine in health and in renal disease" by Reyes, Alvaro A. et al, *Am. J. Physiol.* 267 F331–F346 1994), and deemed particularly beneficial for glomerular function, the product is fortified with arginine, making it more available, because free amino acids having molecular weights of less than about 500 are rapidly absorbed. Other necessary elemental ingredients, e.g. minerals, vitamins and protein may be added as desired, and even additional free amino acids, as long as the following critical properties of the final product are met: pH in a slightly acidic or neutral range e.g. in the range from about 6 to about 8, osmolality below 1000 mOsm/kg water, and viscosity less than 100 cp.

Since a hemodialysis patient averages three treatments per week, or once every 56 hours, though the typical patient is not treated after equal intervals, it is essential that the level of arginine in the bloodstream be maintained. L-arginine is deemed an essential amino acid in patients with renal failure because of the role it plays in the synthesis of endothelium-derived relaxing factor, bacterial killing by macrophages, and production of polyamines (see "Amino Acid Profile and Nitric Oxide Pathway in Patients on Continuous Ambulatory Peritoneal Dialysis: L-Arginine Depletion in Acute Peritonitis" by Heesuk Suh, Tatyana Peresleni, et al *Am. Jour. Kidney Diseases,* Vol 29, No 5 (1997), pp 712–719). Arginine deficiency is suggested as a cause for several aspects of the uremic syndrome, such as impaired blood pressure control, atherogenesis, vascular smooth muscle cell proliferation, macrophage toxicity, and impaired antibacterial defense (see *"Clinical Nutrition—Enteral and Tube Feeding"* by John L. Rombeau and Rolando H. Rolandelli, 3rd edition, pg 448). The maintenance of normal levels of L-arginine depends on the levels of dietary intake of the amino acid. Though the foregoing indicated the beneficial effect of L-arginine, in view of its well-known unpleasant taste, they offered no suggestion as to how arginine in elemental form might be included in a practical, stable liquid nutritional supplement. The problem is to formulate a product with the requisite amount of elemental arginine, yet maintain desirable viscosity and osmolality; also, to imbue it with a good taste, to find the appropriate order of incorporating the components of the recipe to yield desirable organoleptic properties, and to ensure that upon sterilization and packaging, the effectiveness of the arginine is not lost in the product which retains those desirable properties and remains shelf-stable for at least one year.

The composition of this invention is nutritionally complete, by which term is meant that the composition contains adequate nutrients to sustain healthy human life for extended periods. The composition can be cow milk-based, soy-based, or based on other proteins or nutrients, provided it is fortified with at least enough elemental arginine to double the contribution of arginine available from a chosen source of protein. The caloric density of the nutritionally complete composition of the invention contains about 2 cal/ml (calories per milliliter) in a ready-to-feed form. The liquid, nutritionally complete product flows easily under gravity, through a conventional feeding tube, and has tolerable osmolality adapted for an adult enteral composition that is intended to come into contact with the gastric contents of the stomach. Though the product is formulated to be tube-fed, it may also be administered via the normal oral route, and since the latter is preferred, the product's good taste is an important factor. The detrimental effect of bitter elemental arginine on the taste of any formulation containing more than a trace amount had to be overcome. The good taste of the product is provided by the fortuitous effect of one or more carboxylic acids which also function to neutralize the high pH of the arginine. In each formulation, magnesium is provided in the form of magnesium carbonate, magnesium sulfate or magnesium oxide, all deemed undesirable in the '767 formulation (col 10, lines 45–50). In a retorted product, citric acid is essential in combination with citrates of sodium, and/or potassium and/or calcium, and the '767 patent teaches that no citric acid should be used (col 6, lines 43–44).

SUMMARY OF THE INVENTION

L-arginine, which is known to be a non-essential amino acid, is critical for enhancing the glomerular function of the kidneys; and, at least as much elemental arginine is added in a liquid formulation as is present in protein incorporated in the liquid, typically contributing at least about 0.5% of total calories, and preferably from 0.75% to 7% of total calories in the formulation. Because of the combination of a carboxylic acid with elemental arginine, the presterilized liquid formulation has a pH in the range from 6 to 8, preferably from 6.5 to 7.5; a viscosity less than 100 cp, preferably 30 to 70 cp; and an osmolality of less than about 1000 mOsm/kg water, preferably from about 500 to 900 mOsm/kg water. Unexpectedly, combining the L-arginine with one or more specific carboxylic acids not only lowers the pH into the desirable range, but also imbues the product for oral ingestion with a pleasant taste which may be enhanced by other ingredients of the nutritionally complete composition. In the "oral" formulation, neutralizing the arginine with lactic, adipic or malic acids, which are examples of "arginine-neutralizing acids", suppresses the bad taste of arginine, lowers the pH and provides a key ingredient which controls viscosity; varying the levels of staple nutrient components within allowable ranges has surprisingly little effect on the taste, but influences other properties substantially. The formulation is stabilized without the use of commonly used protein stabilizers, and is aseptically sterilized at a temperature below 300° F. for from 3 to 10 sec. In the formulation for a retorted product, neutralizing the arginine with a combination of citric acid and citrates (which act as a buffer), in a citric/citrate ratio in the range from 2 to 8, preferably from 2.5 to 6, both lowers the pH into the desired range as well as stabilizes the protein so that it survives high temperature sterilization in the range from 250° F. to 270° F. for from 10 to 20 min.

This nutritional product is calorie and nutrient-dense, has moderate to high protein content, and a high calcium to phosphorus ratio of at least 1:1, preferably in the range from about 1:1 to 2:1. The product contains about 100 g fat/L, about 200 g carbohydrate/L, and essentially no sugars such as sucrose, lactose or fructose which have an inordinately high adverse effect on osmolality. If desired, a small amount of fructose, contributing less than 1.5% of total calories, may be added provided the desired osmolality of the formulation is maintained. In addition, 8 fl oz of the product which provides about 475 cal, contains from 25 mg to 75 mg of magnesium, and 1 liter meets at least 100% of the RDI (reference daily intake) for vitamins and minerals with the exception of chloride, vitamin D, vitamin A, phosphorus, magnesium, chromium and molybdenum. Yet, the product meets the nutritional requirements of a renal patient. Specifically the product is low in phosphorus content and contains L-arginine to help maintain a desirable normal level for each patient.

A specific product which provides about 2 cal/ml is characterized by having less than 80% by weight water, and the addition of enough elemental arginine to contribute from about 0.75% to 3% total calories. The balance of arginine may be derived from caseinates. The caloric distribution for such a product is as follows: from all arginine 1.2% to 3%; from protein, 12 to 18%; from fat, 40 to 46%; the balance from carbohydrates. In one preferred formulation flavored for oral use, containing essentially no sucrose, lactose or fructose, and lactic acid as taste-suppressant, for those patients who tend to absorb aluminum-containing phosphate binders which are prescribed, no citric acid or citrates are present; in another formulation for tube feeding, containing a combination of citric acid and citrates as taste-suppressant, essentially no lactose, sucrose or fructose is present. Citrates are chosen from the salts of sodium, potassium and calcium to provide a desired balance of the levels of each. Most preferably, a citric acid and citrates-containing formulation is packaged in a retortable container for tube feeding, being hermetically sealed, sterilized and shelf-stabilized at about 256° F. for 13 min. An aseptically sterilized container is sterilized at about 280° F. for 4.5 sec, for oral or tube feeding a product with no citric acid or citrates. In each product, changing the order of addition of the arginine relative to the protein and carbohydrates, and that of the oils relative to the foregoing, produces an undesirable product.

BRIEF DESCRIPTION OF THE DRAWING

The invention will best be understood by reference to the following detailed description, accompanied with a schematic illustration of preferred process steps for making each embodiment of the product:

FIG. 1 is a flow chart for a process to make product free of citric acid or citrates.

DETAILED DESCRIPTION OF PREFERRED EMBODIMENTS

Figure 2:
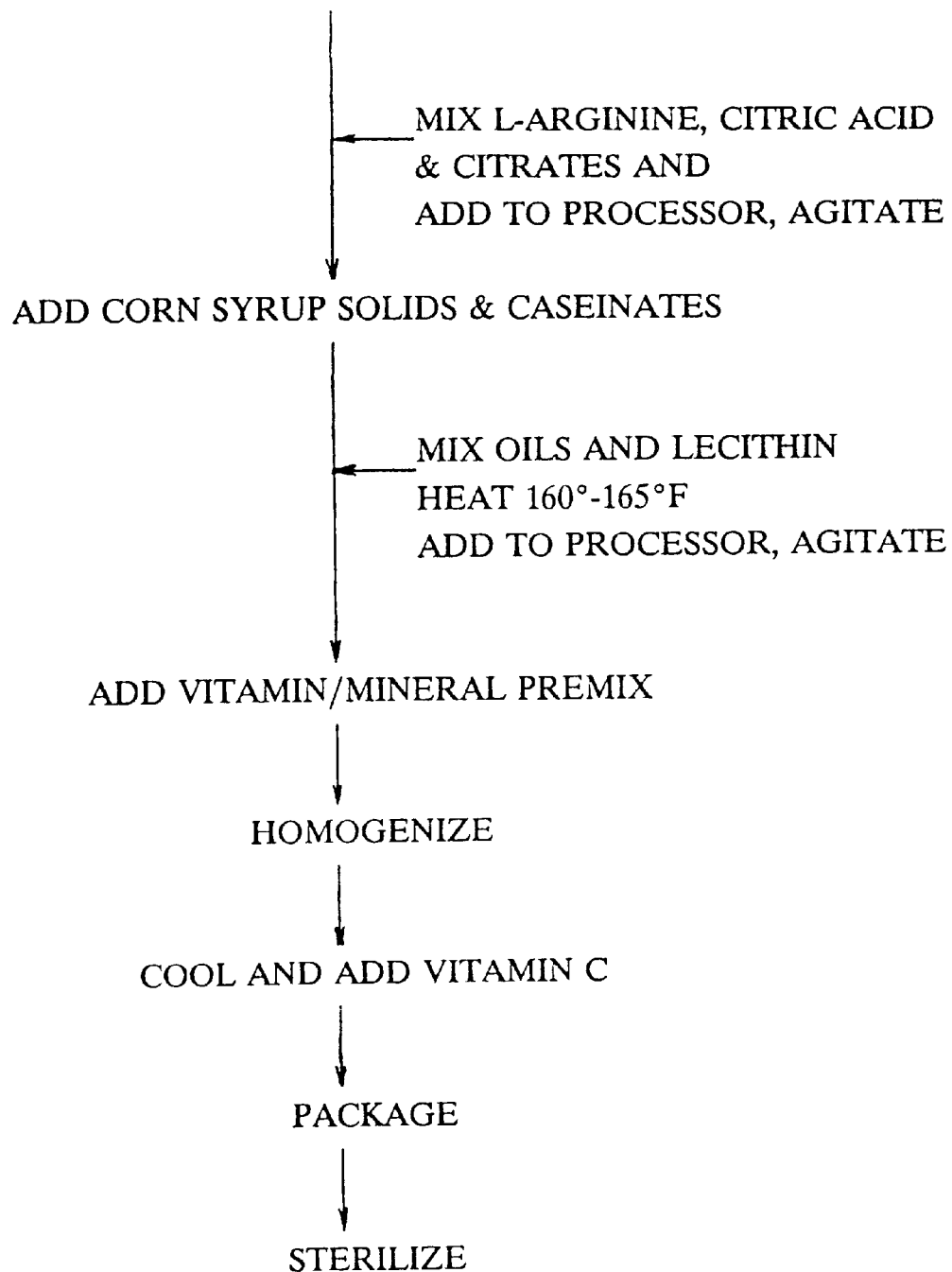
FIG. 2 is a flow chart for a process to make product containing both citric acid and citrates.

Dialyzed patients suffering from renal failure over a prolonged period experience long-term stress and are at risk for malnutrition. The composition, designed to meet the nutritional needs of humans with renal failure, contains ingredients such as a protein (amino acid) source, a lipid source, and a carbohydrate source. Typically milk, skim milk, casein, hydrolyzed casein, hydrolyzed whey protein, whey, whey protein concentrate, vegetable protein concentrate (e.g. soy protein isolate), hydrolyzed vegetable protein (e.g. soy), provide the source of protein, and animal oils, vegetable oils, along with a balanced carbohydrate mix of starch and/or corn syrup solids will supply part or all of the amino acids and/or protein, lipid, and carbohydrate as well as other nutrients such as vitamins and minerals. Sucrose and lactose are excluded because of their adverse effect on the osmolality of the product.

One liter of the product preferably comprises from about 3.7 g to 35 g arginine, about 70 g to 80 g protein, about 90 g to 110 g fat, about 180 g to 220 g carbohydrates and provides about 2000 calories. Most preferably, 1 liter of product comprises 74 g protein, 100 g fat, and 200 g carbohydrate per liter and from 3.7 g to 12.6 g added elemental L-arginine to contribute in the range from 0.75% to 2.5% of total calories respectively.

The water content of the product is less than 80% by weight, preferably less than 70%. If a patient undergoes peritoneal dialysis every 24 hr, the moisture content may be 80%; but if hemodialysis is performed only 3 times a week, the amount of water (when 80% of product is water) ingested in 235.2 fl. oz (4.2 portions, each 8 fl. oz. over 7 days), is much greater relative to the water ingested in 235.2 fl. oz containing less than 70% water. This difference is of great significance with respect to attaining, then maintaining the "dry weight" of the patient between dialysis runs. By "dry weight" is meant the actual body weight at normal hydration. In the most preferred embodiment the volume of water present is about 65% by weight.

The carbohydrate component of the composition of the invention can be any suitable carbohydrate known in the art to be suitable for use in nutritionally complete compositions except added sucrose and lactose. Typical carbohydrates include fructose, xylitol, glucose, maltodextrin, corn syrup, corn syrup solids, rice syrup solids, rice starch, modified corn starch, modified tapioca starch, rice flour, soy flour, and the like. The adverse effects of the carbohydrate (required to be added) on viscosity and osmolality require that corn syrup or corn syrup solids be used in a major amount relative to any other carbohydrate used. It is most preferred to use substantially all corn syrup or corn syrup solids. Fiber may be added as part of the carbohydrate.

The fat (lipid) can be any fat known in the art to be suitable for use in nutritionally complete compositions. Typical lipid sources include milk fat, safflower oil, canola oil, egg yolk lipid, olive oil, cotton seed oil, coconut oil, palm oil, palm kernel oil, soybean oil, sunflower oil, fish oil and fractions of all above oils derived thereof such as palm olein, medium chain triglycerides (MCT), and esters of fatty acids wherein the fatty acids are, for example, arachidonic acid, linoleic acid, palmitic acid, stearic acid, docosahexaneoic acid, eicosapentaneoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil. Most preferred is a combination of high oleic sunflower oil, corn oil and MCT oil because it provides a fat profile which is high in monounsaturated fats, low in saturated fats and the MCT enhances fat absorption.

Preferred protein sources are whey protein, sodium caseinate or calcium caseinate provided available arginine from the protein is supplemented with elemental L-arginine in an amount at least as great as that present in the protein, and preferably from 25% to 600% more than is present in the protein. The protein source can be any protein and/or amino acid mixture known in the art to be suitable for use in nutritionally complete compositions. Typical protein sources are animal protein, vegetable protein such as soy protein, milk protein such as skim milk protein, whey protein and casein, and amino acids (or salts thereof) such as isoleucine, phenylalanine, leucine, lysine, methionine, threonine, tryptophan, arginine, glutamine, taurine, valine, carnitine, tyrosine, serine, and the like.

Elemental arginine is incorporated by neutralization with a carboxylic acid the choice and amount of which depends upon whether the product is to be sterilized at a temperature above that at which the proteins are destabilized, typically above 250° F., if not adequately protected. For aseptic packaging, when the product is to be sterilized at a temperature in the range from 280° F. to 290 for about 10 sec, the arginine is neutralized with an arginine-neutralizing acid selected from the group consisting of lactic acid, malic acid, and adipic acid. The ratio of arginine-neutralizing acid to arginine is in the range from 0.75 to 1.5 for 88% food grade lactic acid. Addition of more than 7% arginine (based on % of total cal) requires so much arginine-neutralizing acid that taste of the product is unacceptable. Since lactic acid is a monocarboxylic acid, malic acid is a hydroxydicarboxylic acid and adipic is a dicarboxylic acid, it is only by chance that they exhibit similar taste and stabilization properties. For the retorted product which is hermetically sealed for tube feeding, when the product is to be stabilized at a temperature in the range from about 250° F. to 270° F. for about 15 min, the arginine is neutralized with a combination of citric acid and citrates of Na, K and Ca, the ratio of citric acid and citrates to arginine being in the range from 1 to 2.5. When the ratio exceeds 2.5, or is less than 1, the stability of the protein is compromised.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Most preferably the product contains the recommended daily allowance (RDA) of nutritional components.

Practitioners also understand that appropriate additional amounts (overages) of vitamin and mineral ingredients need to be provided to compensate for some loss during processing and storage of such compositions. The composition of the invention preferably contains at least 100% of the RDI in 2000 cal of the product with the exceptions noted above.

To select a specific vitamin or mineral compound to be used in the composition requires consideration of that vitamin or compound's chemical nature regarding compatibility with the processing chosen and shelf storage.

Examples of minerals, vitamins and other nutrients optionally present in the formula of the invention include vitamin A, vitamin $B_6$, vitamin $B_{12}$, vitamin E, vitamin K, vitamin C, vitamin D, inositol, taurine, folic acid, thiamine, riboflavin, niacin, biotin, pantothenic acid, choline, calcium, phosphorous, iodine, iron, magnesium, copper, zinc, manganese, chloride, potassium, sodium, β-carotene, nucleotides, selenium, and carnitine. Minerals are usually added in salt form. In addition to compatibility and stability considerations, the presence and amounts of specific minerals and other vitamins will vary somewhat depending on the intended consumer population.

The composition of the invention also typically contains emulsifiers and/or stabilizers such as lecithin, (e.g., egg or soy), carrageenan, xanthan gum, mono- and diglycerides, guar gum, microcrystalline cellulose/carboxymethyl cellulose ("MCC/CMC"), stearoyl lactylates, succinylated monoglycerides, diacetyl tartaric acid esters of monoglycerides, polyglycerol esters of fatty acids, or any mixture thereof.

The composition of the invention can be sterilized, if desired, by techniques known in the art, for example, heat treatment such as autoclaving or retorting, irradiation, and the like, or processed and packaged either by mild aseptic processing for oral feeding, or by more severe sterilization for tube-feeding.

The composition of the invention can be packaged in any type of container known in the art to be useful for storing nutritional products such as glass, lined paperboard, plastic, coated metal cans and the like, but are most preferably packaged in a bottle for tube feeding, and in a paper container for oral use.

The following examples illustrate the invention, but should not be construed as limiting the invention which is defined in the appended claims.

EXAMPLE 1

Referring to FIG. 1 there is presented a process flow diagram for preparing the product in an "aseptic system". In greater detail, an 8000 lb batch of product is prepared as follows:

3756.3 lb of deionized water at 140° F. is pumped into a 1000 gal processing vessel ("processor") and 6 lb of MCC/CMC (familiarly referred to as "gum") added. In a separate oil tank is mixed 523.9 lb H.O. sunflower oil, 110.1 lb MCT oil, and 114.2 lb corn oil and the mixture heated to 100–180° F., preferably 160–165° F. 12.5 lb lecithin is added to the hot oil ("oil mix"). Add 1.6 lb antifoam to the processor and also 440 lb sodium caseinate; 128.7 lb calcium caseinate; 50 lb fructose; and 13.1 lb flavor (vanilla). Add 1744 lb corn syrup solids heated to about 110° F.

In a separate "acid tank" add 20.5 lb lactic acid (commercial 88%) to 200 lb deionized water, add 27.2 lb L-arginine and dissolve. Add to the processor. Add the oil mix to the processor and flush with 100 lb water. Add 3.4 lb choline chloride and 46.5 lb vitamin/mineral premix-708351 with 200 lb water and add to the processor. Flush the acid tank with 200 lb water and add the water to the processor. Heat the mixed product to 140–180° F., preferably 165° F., in a plate heat exchanger and pump to a de-aerator. Commence homogenizing, and after start of homogenization add 150 lb water and 4 lb sodium ascorbate to another tank. Mix to dissolve and add to storage tank. Flush ascorbate tank with 150 lb water. The product is then cooled to a temperature of about 40° F. Agitate continuously until a sample indicates an approved product. Aseptically sterilize at 280° F. for 5 sec in Tetra Brik® packages.

The main ingredients (in lb weight) used to make 8000 lb of aseptic Tetra Brik® product in the above process flow scheme are as follows: deionized water 4756.3; L-arginine 27.2; corn syrup 1744; high oleic sunflower oil 523.9; sodium caseinate 440; calcium caseinate 128.7; corn oil 114.2; MCT oil 110.1; fructose 50; lactic acid 20.5; lecithin 12.5; antifoam 1.6; MCC/CMC ("gum") 6; flavor 13.1; choline chloride 3.4; vitamin/mineral premix 46.5; sodium ascorbate 4.0.

TABLE 1A

The following is a list of ingredients and the relative amounts, in g/liter, typically served in 1 liter of an illustrative embodiment of the product for oral feeding, in which total elemental L-arginine provides 1.2% of total calories:

| | g/liter |
|---|---|
| deionized water | 648.047 |
| 36 DE corn syrup | 237.56 |
| fructose | 6.600 |
| high oleic sunflower oil | 71.380 |
| sodium caseinate | 58.088 |
| calcium caseinate | 19.403 |
| MCT oil | 15.000 |
| corn oil | 15.560 |
| L-arginine | 3.705 |
| lactic acid | 2.787 |

TABLE 1A-continued

The following is a list of ingredients and the relative amounts, in g/liter, typically served in 1 liter of an illustrative embodiment of the product for oral feeding, in which total elemental L-arginine provides 1.2% of total calories:

| | g/liter |
|---|---|
| premix-708351 | 6.34 |
| artificial vanilla flavor | 1.790 |
| lecithin | 1.703 |
| "gum" | 0.812 |
| choline chloride | 0.462 |
| sodium ascorbate | 0.545 |
| antifoam | 0.218 |
| Total | 1090.1 |

TABLE 1B

The following is a list of ingredients in an illustrative embodiment of the vitamin/mineral premix-708351 ("premix") and the relative amounts of each:

| | g/liter |
|---|---|
| calcium carbonate | 2.425 |
| potassium chloride | 1.583 |
| magnesium carbonate | 0.676 |
| tricalcium phosphate | 0.347 |
| carnitine | 0.296 |
| β-carotene | 0.223 |
| taurine | 0.167 |
| α-tocopheryl acetate | 0.117 |
| selenium yeast | 0.115 |
| biotin | 0.080 |
| zinc sulfate | 0.070 |
| ferrous sulfate | 0.061 |
| niacinamide (B3) | 0.044 |
| calcium pantothenate | 0.028 |
| manganese sulfate | 0.018 |
| cyanocobalamin B12 | 0.016 |
| copper gluconate | 0.016 |
| phytonadione (vitamin K) | 0.014 |
| pyridoxine HCl | 0.014 |
| folic acid | 0.012 |
| Vitamin A palmitate | 0.007 |
| thiamin HCl (B1) | 0.006 |
| potassium iodide | 0.006 |
| riboflavin (B2) | 0.004 |
| cholecalciferol (D) | 0.001 |
| Total | 6.34 |

EXAMPLE 2

Referring to FIG. 2 there is presented a process flow diagram for preparation of the product in a retort system. In greater detail, a 10000 lb batch of product is prepared as follows:

4190.7 lb of hot deionized water at above 100° F. and up to 180° F. is pumped into a 1000 gal processor and 2.0 lb antifoam added along with 7.5 lb "gum". Add 33.7 lb citrates, 13.7 lb citric acid and 44.2 lb L-arginine to the processor and agitate on high for about 10 minutes. Then add 532.9 lb sodium caseinate, 178 lb calcium caseinate, 1900 lb corn syrup solids, and 60.6 lb fructose. Flush lines with DI water, add to the processor and heat to a temperature below 165° F., preferably in the range from 150°–160° F. In a first oil slurry tank, mix 137.6 lb MCT oil, 142.8 lb corn oil and 200 lb high oleic sunflower oil and commence heating. When the oil reaches 140–180° F., preferably 160–165° F., add 15.6 lb soy lecithin. In a second oil slurry tank pour 454.9 lb high oleic sunflower oil and heat to 140–180° F., preferably 160–165° F. Add the contents of the two oil slurry tanks to the processor and maintain the temperature of its contents in the range 130–180° F., preferably at about 165° F. Add 300 lb DI water and 81.7 lb of vitamin/mineral premix 280-23. In a 10 gal vessel containing 50 lb DI water at room temperature mix 4.2 lb choline chloride. Add to the dissolved premix-280-23, and add to the processor. Homogenize the mixture through a two-stage homogenizer, cool and store the cooled homogenized product in a storage tank. If desired, the mixture may be homogenized a second time. Add 5.0 lb ascorbate and agitate to disperse.

The homogenized product is packaged, preferably in 1 liter plastic bottles. The bottles are preferably sterilized by immersing the bottles in water at 250° F. and agitating them end-over-end for about 19 min.

The main ingredients (in lb weight) used to make 10000 lb of a specific embodiment of the product for tube feeding in the above process flow scheme are as follows: deionized water 6190.7; L-arginine 44.2; corn syrup solids 1900; high oleic sunflower oil 654.9; sodium caseinate 532.9; calcium caseinate 178; corn oil 142.8; MCT oil 137.6; fructose 60.6; citric acid 13.7; citrates 33.7; soy lecithin 15.6; antifoam 2.0; "gum" 7.5; choline chloride 4.2; vitamin/mineral premix-280-23 81.7; and, sodium ascorbate 5.0

TABLE 2A

The following is a list of ingredients and the relative amounts of each, in a first illustrative embodiment of the product for tube feeding in which total elemental L-arginine provides about 1.2% of total calories:

|  | g/liter |
|---|---|
| deionized water | 674.787 |
| corn syrup solids | 206.550 |
| high oleic sunflower oil | 71.380 |
| sodium caseinate | 58.088 |
| calcium caseinate | 19.403 |
| MCT oil | 15.000 |
| corn oil | 15.560 |
| L-arginine | 4.816 |
| premix-280-23 | 8.900 |
| fructose | 6.600 |
| sodium citrate | 2.882 |
| lecithin | 1.703 |
| citric acid | 1.495 |
| "gum" | 0.812 |
| potassium citrate | 0.800 |
| choline chloride | 0.462 |
| sodium ascorbate | 0.545 |
| antifoam | 0.218 |
| Total | 1090.00 |

TABLE 2B

The following is a list of ingredients in an illustrative embodiment of the vitamin/mineral premix-280-23 and the relative amounts of each:

|  | g/liter |
|---|---|
| calcium citrate | 4.445 |
| potassium chloride | 1.642 |
| magnesium sulfate | 0.755 |
| tricalcium phosphate | 0.346 |
| carnitine | 0.307 |
| β-carotene | 0.223 |
| magnesium oxide | 0.200 |
| maltodextrin | 0.180 |
| taurine | 0.167 |
| α-tocopherylacetate | 0.117 |
| selenium yeast | 0.115 |

TABLE 2B-continued

The following is a list of ingredients in an illustrative embodiment of the vitamin/mineral premix-280-23 and the relative amounts of each:

|  | g/liter |
|---|---|
| biotin | 0.080 |
| zinc sulfate | 0.070 |
| ferrous sulfate | 0.061 |
| niacinamide (B3) | 0.043 |
| calcium pantothenate | 0.027 |
| magnesium sulfate | 0.018 |
| cyanocobalamin B12 | 0.016 |
| copper gluconate | 0.016 |
| phytonadione (vitamin K) | 0.014 |
| pyridoxine HCl | 0.014 |
| folic acid | 0.012 |
| Vitamin A palmitate | 0.007 |
| thiamin HCl (B1) | 0.006 |
| potassium iodide | 0.006 |
| riboflavin (B2) | 0.004 |
| cholecalciferol (D) | 0.001 |
| Total | 8.90 |

TABLE 2C

The following is a list of ingredients and the relative amounts of each, in a second illustrative embodiment of the product for tube feeding in which total elemental L-arginine provides about 1% of total calories:

|  | g/liter |
|---|---|
| deionized water | 645.480 |
| liquid corn syrup | 238.408 |
| fructose | 6.600 |
| high oleic sunflower oil | 71.380 |
| sodium caseinate | 58.088 |
| calcium caseinate | 19.403 |
| MCT oil | 15.000 |
| corn oil | 15.560 |
| L-arginine | 3.705 |
| premix 267-129 | 3.010 |
| calcium citrate | 4.445 |
| potassium chloride | 1.642 |
| lecithin | 1.703 |
| choline chloride | 0.462 |
| sodium ascorbate | 0.273 |
| antifoam | 0.218 |
| "gum" | 0.812 |
| citric acid | 1.150 |
| β-carotene | 0.223 |
| sodium citrate | 2.482 |
| Total | 1090.05 |

TABLE 2D

The following is a list of ingredients and the relative amounts of each, in a third illustrative embodiment of the product for tube feeding in which total elemental L-arginine provides about 2% of total calories:

|  | g/liter |
|---|---|
| deionized water | 645.850 |
| liquid corn syrup | 238.408 |
| fructose | 6.600 |
| high oleic sunflower oil | 71.380 |
| sodium caseinate | 54.900 |
| calcium caseinate | 18.523 |
| MCT oil | 15.000 |
| corn oil | 15.560 |
| L-arginine | 7.410 |
| premix 267-129 | 3.010 |
| calcium citrate | 4.445 |

TABLE 2D-continued

The following is a list of ingredients and the relative amounts of each, in a third illustrative embodiment of the product for tube feeding in which total elemental L-arginine provides about 2% of total calories:

|  | g/liter |
| --- | --- |
| potassium chloride | 1.642 |
| lecithin | 1.703 |
| choline chloride | 0.462 |
| sodium ascorbate | 0.273 |
| antifoam | 0.218 |
| "gum" | 0.812 |
| citric acid | 2.300 |
| β-carotene | 0.223 |
| sodium citrate | 1.282 |
| Total | 1090.00 |

TABLE 2E

The following is a list of ingredients and the relative amounts of each, in a fourth illustrative embodiment of the product for tube feeding in which total elemental L-arginine provides about 3% of total calories:

|  | g/liter |
| --- | --- |
| deionized water | 648.430 |
| liquid corn syrup | 236.915 |
| fructose | 6.600 |
| high oleic sunflower oil | 71.380 |
| sodium caseinate | 50.819 |
| calcium caseinate | 16.980 |
| MCT oil | 15.000 |
| corn oil | 15.560 |
| L-arginine | 12.602 |
| premix 267-129 | 3.010 |
| calcium citrate | 4.445 |
| potassium chloride | 1.642 |
| lecithin | 1.703 |
| choline chloride | 0.462 |
| sodium ascorbate | 0.273 |
| antifoam | 0.218 |
| "gum" | 0.812 |
| citric acid | 2.930 |
| β-carotene | 0.223 |
| Total | 1090.01 |

TABLE 2F

The following is a list of ingredients in an illustrative embodiment of the vitamin/mineral premix 267-129 and the relative amounts of each:

|  | g/liter |
| --- | --- |
| magnesium sulfate | 1.511 |
| tricalcium phosphate | 0.346 |
| carnitine | 0.307 |
| taurine | 0.167 |
| α-tocopherylacetate | 0.117 |
| selenium yeast | 0.115 |
| biotin | 0.080 |
| zinc sulfate | 0.070 |
| ferrous sulfate | 0.061 |
| maltodextrin | 0.047 |
| niacinamide (B3) | 0.044 |
| calcium pantothenate | 0.027 |
| manganese sulfate | 0.018 |
| cyanocobalamin B12 | 0.016 |
| copper gluconate | 0.016 |
| phytonadione (vitamin K) | 0.014 |
| pyridoxine HCl | 0.014 |
| folic acid | 0.012 |
| Vitamin A palmitate | 0.007 |

TABLE 2F-continued

The following is a list of ingredients in an illustrative embodiment of the vitamin/mineral premix 267-129 and the relative amounts of each:

|  | g/liter |
| --- | --- |
| thiamin HCl (B1) | 0.006 |
| potassium iodide | 0.006 |
| riboflavin (B2) | 0.004 |
| cholecalciferol (D) | 0.001 |
| Total | 3.01 |

In the foregoing examples, a very small amount of fructose is used for flavor, despite its adverse effect on osmolality. Substituting maltodextrin would relieve the problem with excess osmolality. To the extent that the addition of sucrose or lactose can be tolerated for their adverse effect on osmolality, small amounts of either may be used, but less than the amount of fructose used in the foregoing examples.

We claim:

1. A liquid nutritional composition for enhancing the kidney glomerular function, comprising added L-arginine, an arginine-neutralizing acid, protein, fat, carbohydrates, vitamins and minerals, wherein said added L-arginine contributes from 0.5% to 7% of total calories of said composition, said acid is selected from the group consisting of lactic acid, malic acid, adipic acid, and mixtures thereof, and said acid is added in a range sufficient to render said composition to have a pH from 6 to 8.

2. The composition according to claim 1 wherein the composition has a caloric density of about 2 cal/ml.

3. The composition according to claim 1 wherein the L-arginine contributes from about 1.2% to 3% of total calories.

4. The composition according to claim 1 wherein the composition has an osmolality from about 500 to about 900 mOsm/kg water.

5. A liquid nutritional composition for enhancing the kidney glomerular function, comprising added L-arginine, citric acid in combination with citrate, protein, fat, carbohydrates, vitamins and minerals, wherein said composition has a pH between 6 and 8, said composition has a weight ratio of citric and citrate to arginine between 1 and 2.5, said added L-arginine contributes from 0.5% to 7% of total calories of said composition, and said citrate is selected from the group consisting of citrates of sodium, potassium and calcium, and wherein said composition is adapted for retort sterilization.

6. An aseptically packaged liquid nutritional composition for oral ingestion, comprising added L-arginine, an arginine-neutralizing acid, protein, fat, carbohydrates, vitamins and minerals, wherein said acid is selected from the group consisting of lactic acid, malic acid, adipic acid and mixtures thereof, said composition has a pH between 6 and 8, and said added L-arginine contributes from 0.5% to 7% of total calories of said composition.

7. A retort sterilized nutritional composition for enhancing the glomerular function of diseased kidneys, comprising added L-arginine, citric acid, citrate, protein, fat, carbohydrates, vitamins and minerals, wherein said composition has a pH between 6 and 8, said composition has a weight ratio of citric and citrate to arginine between 1 and 2.5, said added L-arginine contributes from 0.5%% to 7% of total calories of said composition, and said citrate is selected from the group consisting of citrates of sodium, potassium or calcium.

* * * * *